US006716239B2

(12) United States Patent
Sowinski et al.

(10) Patent No.: US 6,716,239 B2
(45) Date of Patent: Apr. 6, 2004

(54) EPTFE GRAFT WITH AXIAL ELONGATION PROPERTIES

(75) Inventors: Krzysztof Sowinski, Wallington, NJ (US); Jamie Henderson, Oakland, NJ (US); Howard Woleck, Morris Plains, NJ (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/898,415

(22) Filed: Jul. 3, 2001

(65) Prior Publication Data

US 2003/0009210 A1 Jan. 9, 2003

(Under 37 CFR 1.47)

(51) Int. Cl.[7] .................................................. A61F 2/06
(52) U.S. Cl. ........................ 623/1.13; 600/36; 623/1.51; 623/1.53
(58) Field of Search ........................... 623/1, 1.13, 1.5, 623/1.51, 1.52, 1.53; 600/36

(56) References Cited

U.S. PATENT DOCUMENTS

| 4,082,893 | A |   | 4/1978  | Okita |
|-----------|---|---|---------|-------|
| 4,104,394 | A |   | 8/1978  | Okita |
| 4,332,035 | A |   | 6/1982  | Mano |
| 4,347,204 | A |   | 8/1982  | Takagi et al. |
| 4,553,545 | A |   | 11/1985 | Maass et al. |
| 4,655,771 | A |   | 4/1987  | Wallsten |
| 4,713,070 | A |   | 12/1987 | Mano |
| 4,743,480 | A |   | 5/1988  | Campbell et al. |
| 4,830,484 | A |   | 5/1989  | Yamamoto et al. |
| 4,876,051 | A |   | 10/1989 | Campbell et al. |
| 4,877,661 | A |   | 10/1989 | House et al. |
| 5,061,275 | A | * | 10/1991 | Wallsten |
| 5,437,900 | A |   | 8/1995  | Kuzowski |
| 5,466,509 | A |   | 11/1995 | Kowligi et al. |
| 5,474,824 | A |   | 12/1995 | Martakos et al. |
| 5,527,353 | A |   | 6/1996  | Schmitt |
| 5,718,973 | A |   | 2/1998  | Lewis et al. |
| 5,788,626 | A |   | 8/1998  | Thompson |
| 5,957,962 | A |   | 9/1999  | Wallsten et al. |
| 6,039,755 | A |   | 3/2000  | Edwin et al. |
| 6,402,779 | B1 |  | 6/2002  | Colone et al. |
| 6,436,135 | B1 | * | 8/2002 | Goldfarb |

* cited by examiner

Primary Examiner—Nicholas D. Lucchesi
Assistant Examiner—Lalita M Hamilton
(74) Attorney, Agent, or Firm—Hoffmann & Baron, LLP

(57) ABSTRACT

An improved ePTFE material and method of preparing the improved ePTFE material provides a tubular structure with enhanced axial elongation, radial expansion, and physical recovery characteristics.

24 Claims, 4 Drawing Sheets

EPTFE GRAFT WITH AXIAL ELONGATION PROPERTIES

FIELD OF THE INVENTION

The present invention is generally directed to an ePTFE article having enhanced physical recovery properties. More particularly, the present invention relates to an ePTFE tube with enhanced axial elongation and recovery properties.

BACKGROUND OF THE INVENTION

The use of ePTFE grafts and ePTFE stent/grafts for intraluminal repair is known in the art. Expanded polytetrafluoroethylene grafts as well as ePTFE stent/grafts, or covered stents, may be implanted in a radially compressed state generally using a catheter into a blood vessel, or virtually any body chamber in the body. The graft or expandable covered stent is typically positioned and released from a delivery catheter at a damaged area as desired. In the case of covered stents, a stent is often contained within an ePTFE graft, the stent providing outward pressure and support for the body lumen walls. The addition of the cover on the stent acts to reduce cell growth and occlusions in the interior of the lumen.

Grafts and covered expandable stents that are known in the art are disclosed in the following documents: U.S. Pat. No. 3,953,566 to Gore; U.S. Pat. No. 4,655,771 to Wallsten; U.S. Pat. No. 5,061,275 to Wallsten et al.; U.S. Pat. No. 5,112,900 to Buddenhagen et al.; U.S. Pat. No. 5,123,917 to Lee; U.S. Pat. No. 5,282,823 to Schwartz et al.; U.S. Pat. No. 5,282,824 to Gianturco; U.S. Pat. No. 4,850,999 to Plank; European Patent Application No. 0 621 015 A1 to Lukic; European Patent Application No. 0 551 179 A1 to Palmaz; DE 3918736 A1 to Vallbracht; Patent Cooperation Treaty Application WO 95/05131 to Gore, Patent Cooperation Treaty Application WO 95/05132 to Gore; Patent Cooperation Treaty Application WO 95/05555 to Gore; Patent Cooperation Treaty Application WO 87/04935 to Michelle. All documents cited herein, including the foregoing, are incorporated herein in their entireties for all purposes.

It is desirable, however, to provide a stent covering which expands and contracts in concert with an underlying stent. Some stents in particular undergo extreme axial elongation when radially compressed to a reduced diameter. When the diameter expands however, to its expanded state, the stent longitudinally shortens. Such a stent is accordingly loaded in a radially compressed and axially elongated state, and implanted by radially enlarging the stent to its implantation diameter.

Coverings of such stents are often insufficient as they fail to fully and completely flex and remain intact with a stent with exaggerated dimensions. A stent which shows such exaggerated axial elongation in accordance with radial shortening is shown in the above referenced Wallsten U.S. Pat. Nos. 4,655,771, and 5,061,275.

Expanded polytetrafluoroethylene is not an elastomeric material. It is therefore not in ePTFE's nature to return to an original state after it has been stretched. It is therefore difficult to use an ePTFE covering with such stents of exaggerated axial and radial variations as mentioned above because ePTFE is not able to stretch and recover in concert with the stent, for example PTFE is not readily plastically deformable. Methods of treating ePTFE have been developed, however, in order to enhance ePTFE's physical expansion and recovery characteristics.

For example, U.S. Pat. No. 4,877,661 to House et al. discloses an ePTFE which is formed by extruding, compressing, heating, cooling and then stretching it back to its original length. The microstructure of the porous ePTFE material consists of nodes interconnected by fibrils; substantially all the fibrils having a bent or wavy appearance. The bent structure allegedly provides the ePTFE with properties of "rapid recovery"; i.e. when the ePTFE tube is pulled, the fibrils then have a tendency to return to the bent state.

U.S. Pat. No. 6,039,755 to Edwin et al. discloses an ePTFE tube which is used as an implant. The tube is implanted and radially expanded in vivo, and such radial expansion deforms the ePTFE material by elongating its nodes past the elastic deformation of the ePTFE.

U.S. Pat. No. 5,788,626 to Thompson discloses an expandable stent/graft with an ePTFE cover, the ePTFE cover having a bi-axially oriented node-fibril structure with folded fibrils.

U.S. Pat. No. 4,830,862 to Yamamoto et al. discloses a heat shrinkable tetrafluoroethylene polymer tube which is radially expanded, and serves to make a tube which will heat shrink around another article to form a composite article with a tetrafluoroethylene cover heat-shrunk thereto.

While the above referenced patents attempt to address the need for an ePTFE composition with recovery properties, they fall short in providing an ePTFE covering capable of stretching and recovering in concert with a stent having extreme radial expansion and axial elongation properties, such as those described stents in the Wallsten patents listed above. There is a need for an ePTFE material which has the capability of dimensional changes in the axial and radial direction, without substantial plastic deformation of the material or without substantially changing the fibril length. The present invention is therefore directed to overcoming the drawbacks and deficiencies of the prior art.

SUMMARY OF THE INVENTION

It is therefore an advantage of the present invention to provide an ePTFE tubular structure with enhanced longitudinal elongation and radial expansion properties.

It is also an advantage of the present invention to provide an ePTFE tubular structure with enhanced longitudinal elongation properties and radial expansion properties as well as physical recovery properties.

It is also an advantage of the present invention to provide an improved ePTFE vascular stent/graft combination. More particularly it is desirous to provide an ePTFE covered stent in which the covering has the ability to expand and contract in accordance with the stent.

It is a further advantage of the present invention to provide a novel method of increasing ePTFE's physical recovery characteristics.

In the efficient attainment of these and other advantages, the present invention provides an ePTFE tubular structure having a first node and fibril orientation characterized by longitudinal expansion of said tubular structure and a second node and fibril orientation wherein the fibrils of the second orientation have been hingeably rotated about the nodes of the ePTFE. The second node and fibril orientation is formed after physical alteration of the first orientation occurs without a substantial change in length of the fibrils and provides the ePTFE tubular structure with enhanced longitudinal elongation and radial expansion properties.

The method of making the ePTFE tubular structure is also disclosed. The method consists of first forming a tube of polytetrafluoroethylene, then longitudinally stretching the polytetrafluoroethylene tube to form an expanded polytetrafluoroethylene (ePTFE) tube. The ePTFE tube is comprised of fibrils oriented in a longitudinal direction of the tube and nodes of a first length oriented in a circumferential direction of the tube. The ePTFE tube is then placed circumferentially exterior to a longitudinal foreshortening and radial expansion device. The ePTFE tube is then radially expanded with radial pressure from the foreshortening expansion mechanism to skew the fibrils and lengthen the nodes to a second length, the second node length being greater than the first node length, and the fibrils of the ePTFE become oriented non-longitudinally. The reoriented structure provides an ePTFE tubular structure with increased longitudinal elongation and radial expansion and recovery properties.

DETAILED DESCRIPTION OF THE INVENTION

The ePTFE material of the present invention is used to construct a physically modified ePTFE tubular structure having enhanced axial elongation and radial expansion properties. The ePTFE tubular structure is especially advantageous to be used in conjunction with a stent with exaggerated axial elongation and radial expansion properties. The ePTFE tubular structure of the present invention is preferably used as a cover in a covered stent, or other endoprosthesis suitable for intraluminal or endoscopic delivery.

The term hingeably rotated as used herein refers to reorientation of previously uniformly oriented line segments by a change in position of one end of each line segment in relation to the other end of each segment, which remains fixed; i.e., the "hinge" about which the other end rotates. The reorientation takes place without a substantial change in dimension of the line segment.

The ePTFE tubular structure of the present invention has enhanced longitudinal elongation and radial expansion, as well as physical recovery properties. The ePTFE tubular structure is able to be elongated or expanded and then returned to its original state. The ePTFE tubular structure is able to return to its original state without a substantial elastic force existing within the ePTFE material. The term elastic as used herein refers to a material which exhibits a tendency to rebound or assume its original shape, and the force associated with the material's inherent tendency to assume its original shape or dimension; i.e. when stretching an elastic material, the material wants to return to its original shape, and therefore exerts a force directing its return to that original shape.

It may also be said that the ePTFE tubular structure of the present invention be treated and altered in such a way that there is significantly less plastic deformation than traditionally re-expanded processes. In other words, the ePTFE is treated in such a manner that the significantly less plastic deformation of the ePTFE leads to this unexpected product which possess enhanced longitudinally elongation and radial expansion properties, as well as the ability to physically recover from the elongated and expanded state.

Figure 1:
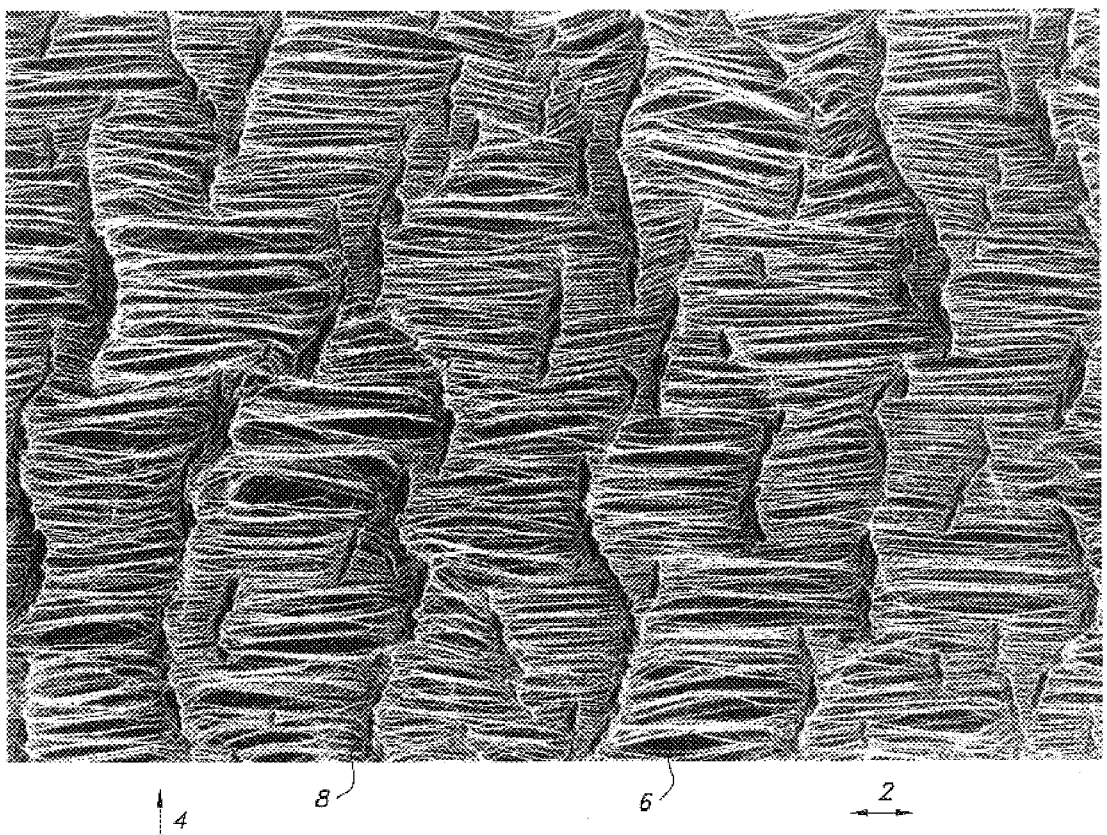
FIG. 1 is a photomicrograph showing a longitudinally expanded ePTFE structure which constitutes the prior art.

Referring now to FIG. 1 of the drawings, a photomicrograph of a traditionally longitudinally expanded ePTFE tubular structure is shown. The tube has been stretched in the longitudinal direction shown by directional arrow 2, leaving the nodes circumferentially oriented in circumferential direction shown by the directional arrow 4. Such a longitudinally expanded ePTFE structure is well known in the art. The fibrils 6 are shown as being uniformly oriented in the longitudinal direction shown by directional arrow 2. Nodes 8 are shown and are uniformly oriented in circumferential direction 4.

Figure 2:
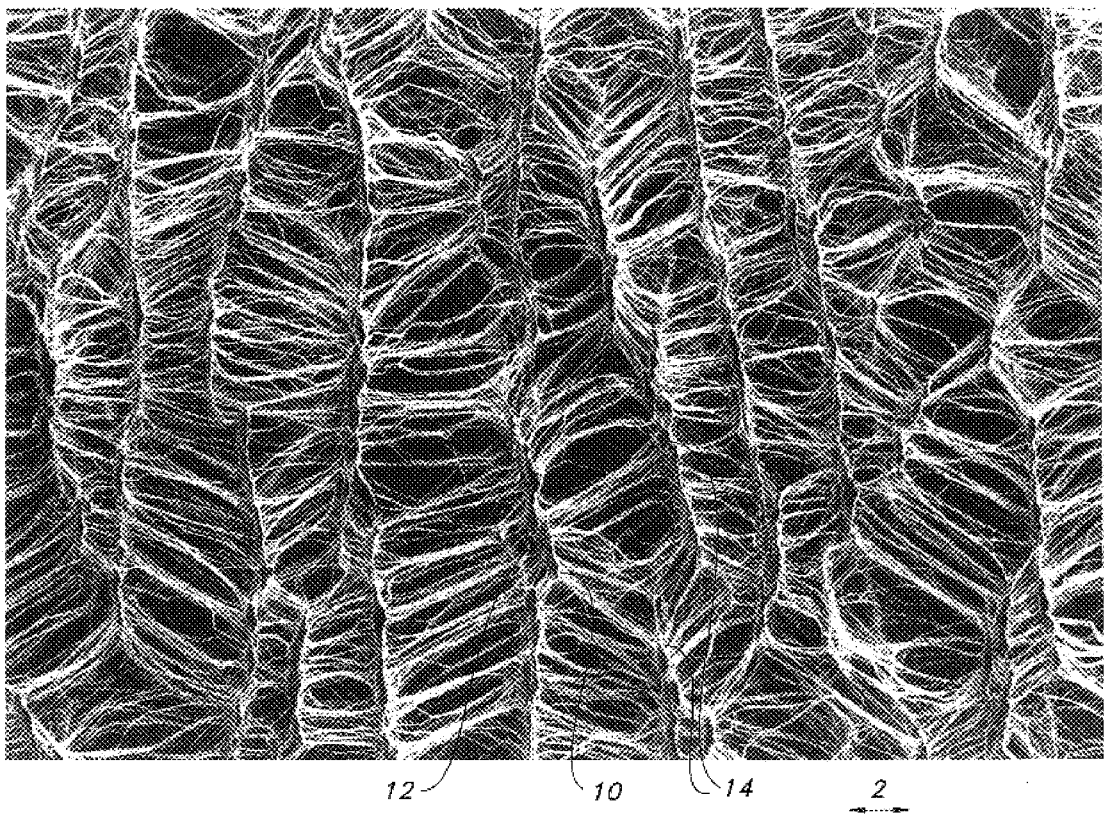
FIG. 2 is a photomicrograph of an ePTFE tubular structure of the present invention showing hingeably rotated fibrils.

With reference now to FIG. 2 of the drawings a photomicrograph of the ePTFE tubular structure of the present invention is shown. Nodes 10 are shown in the photomicrograph with a set of fibrils with first ends 12 and second ends 14 attached thereto. The fibrils with first ends 12 and second ends 14 are shown in a hingeably rotated position. With reference now to FIG. 1 of the drawings, previous fibril structures 6 were shown to be substantially longitudinally oriented parallel to longitudinal axis 2. FIG. 2 shows the fibrils as reoriented, or hingeably rotated so that they are not substantially longitudinally oriented in the direction shown by directional arrow 2.

The fibrils have first ends 12 which in FIG. 2 are fixed to node 10. Second ends 14 of the fibrils are hingeably rotated after the method of the present invention has been performed on the ePTFE tubular structure. Nodes 10 have been lengthened to a second length greater than the first length of the pretreated nodes. While the nodes have been somewhat lengthened to a second length, the ePTFE tubular structures of the present invention do not require lengthening of the nodes. The hingeable rotation, or skewing of the fibrils provides the enhanced stretch and recovery properties of the present invention.

Figure 3:
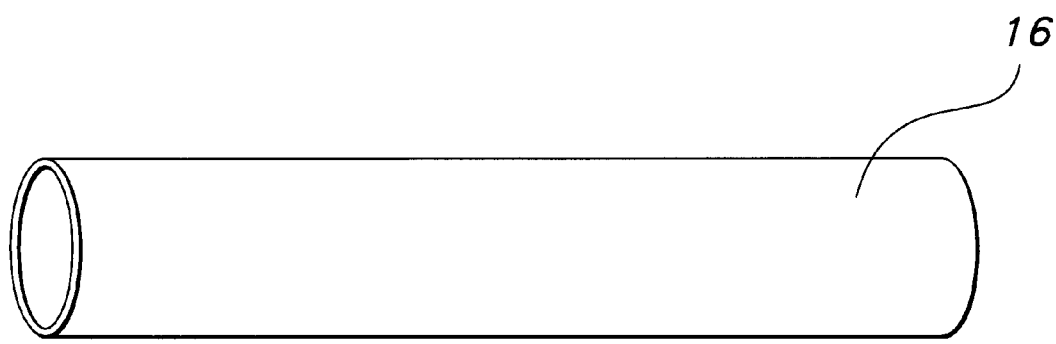
FIG. 3 is a schematic drawing showing the ePTFE tubular structure of the present invention in a longitudinally extended configuration.
Figure 4:
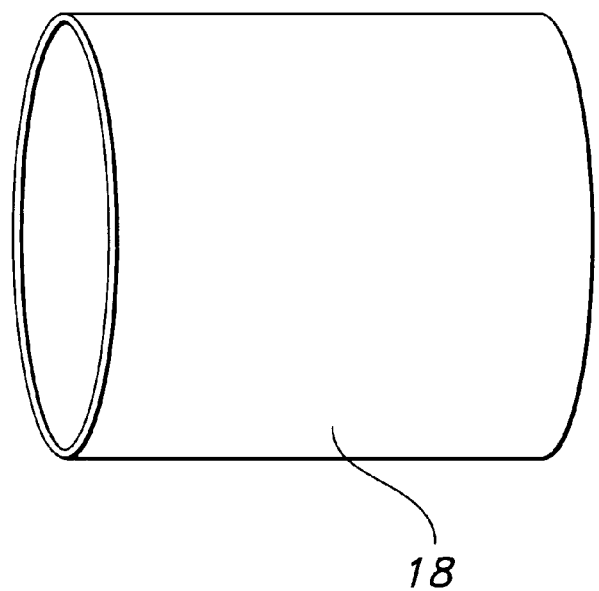
FIG. 4 is a schematic drawing showing the tubular structure of FIG. 3 in a relaxed state.

The ePTFE tubular structure of the present invention possesses a first longitudinal length and a first radius in a relaxed state. The term relaxed state as used herein refers to the ePTFE tubular structure at rest when no forces are exerted thereto; whether radially, longitudinally, or otherwise directed forces. The ePTFE tubular structure of the present invention also possesses a second longitudinal length and a second radius when not in a relaxed state, wherein the second longitudinal length is greater than the first longitudinal length and the second radius is less than the first radius. This can be seen with reference to FIGS. 3 and 4 of the drawings. FIG. 3 is a schematic showing the tubular structure of the present invention in a longitudinally expanded state and circumferentially compressed state. FIG. 4 of the drawings is a schematic showing the same tubular structure in a longitudinally compressed and radially expanded state. In its relaxed state, the ePTFE tubular structure 18 in FIG. 4 is radially expanded and longitudinally shortened. The second longitudinal length of the ePTFE tubular structure may be up to 800% or more of the first length of the tubular structure.

Figure 5:
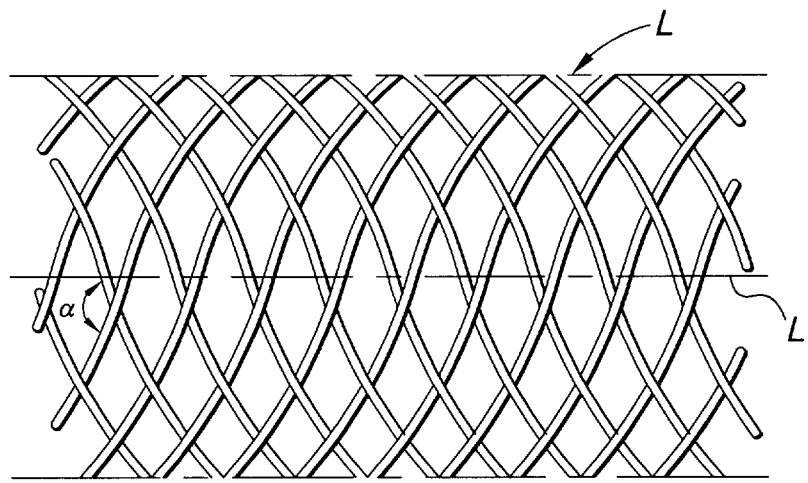
FIG. 5 is a schematic drawing showing a radially expanded stent which may be used in the present invention.
Figure 6:
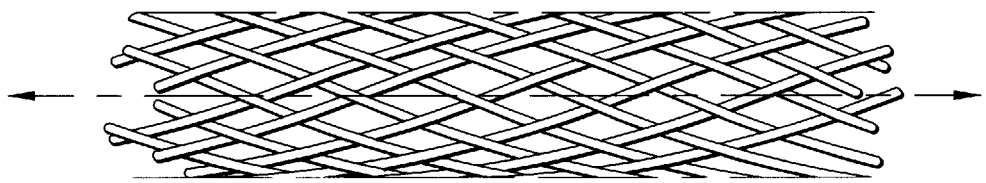
FIG. 6 is a schematic of the stent of FIG. 5 shown in a longitudinally lengthened and radially compressed state of the present invention.

FIGS. 5 and 6 also show the dimensional disparity between the relaxed state as shown in FIG. 5 and the radially compressed state as shown in FIG. 6. FIGS. 5 and 6 show a stent which may be used in the present invention. The ePTFE tubular structure of the present invention may be placed exteriorly, interiorly or both exteriorly and interiorly to the stent shown in FIGS. 5 and 6.

Figure 7:
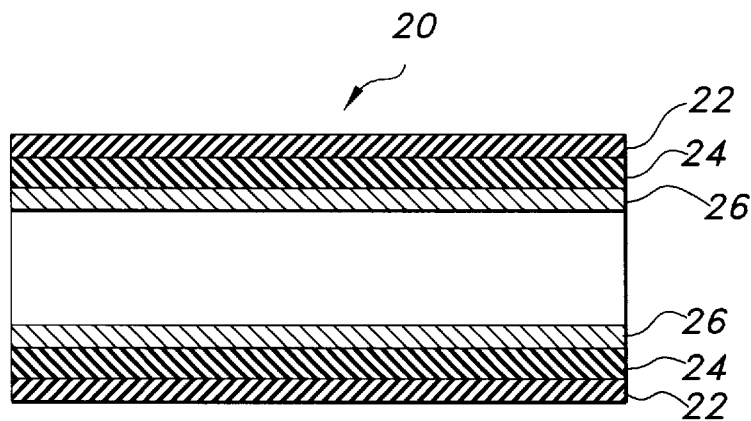
FIG. 7 is a cross-sectional of the present invention which further includes a textile graft layer in addition to ePTFE and stent.

With reference now to FIG. 7 of the drawings, a composite stent-graft 20 is shown in cross-section. The composite stent-graft includes a textile layer 22, the ePTFE tubular structure of the present invention 24, and a stent 26. The stent 26 is shown circumferentially interior to the ePTFE tubular structure and the outer textile layer in FIG. 7. It is, however, contemplated that numerous combinations may be employed in the present invention. The textile layer may be placed on the opposed side of the stent (as compared to the ePTFE tubular structure's position with regard to the stent) or on the same side (interior or exterior of the stent) as shown in FIG. 7.

Although a braided expanding stent is one preferred embodiment of the present invention, the ePTFE tubular structure of the present invention may be used with a variety of different stents. Some stents which may be used, without limitation, include self expanding stents and balloon expandable stents. The stents may be capable of radially contracting or expanding, as well, and in this sense can best be described as radially or circumferentially distensable or deformable. Self expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium, and other biocompatible materials, as well as polymeric stents.

The ePTFE tubular structure of the present invention may be affixed to a stent by a number of different means. The stent may be affixed to a first and second (inner and outer) tubular structure preferably by applying circumferential or radial pressure to the first and second tubular structure after they are loaded onto a mandrel, and heating the resulting assembly to form a mechanical bond between the tubular structures. In another embodiment, the step of affixing the tubular structures to the stent includes the step of applying at least one of a biocompatible adhesive, including but not limited to, a dispersion of polytetrafluoroethylene, fluoroethylenepolypropylene (FEP), polyurethane, polyamide, polyimid or silicone between the tubular structure and the stent, and where a biocompatible adhesive or melt thermoplastic is used, heating the resulting assembly at a melt temperature of the adhesive or melt thermoplastic and below the sintering temperature of the PTFE tubular structure. It is also understood that the biocompatible adhesive may be applied as an interlayer or directly to either of the first or second tubular structures, or to the stent itself. If just one tubular structure is being used the affixing may take place by any of the methods already disclosed.

The stent and tubular structure may have a second longitudinal length in the non-relaxed state which is at least about 1.5 times longer than the first longitudinal length of the relaxed state. In another embodiment of the present invention the second longitudinal length of the ePTFE tubular structure is at least about 2.0 times longer than the first longitudinal length of the relaxed state. In a further embodiment of the present invention, the second longitudinal length may be at least about 2.5 times longer that the first longitudinal length of the relaxed state. Similarly, the tubular structure of the present invention may have a first radius characteristic of its relaxed state which is at least about 1.5 times larger than the second radius of the radially compressed state. In another embodiment, the tubular structure of the present invention may have a first radius in its relaxed state which is at least about 2.0 times larger than the second radius. In a still further embodiment of the present invention, the tubular structure may have a first radius in its relaxed state which is at least about 2.5 times larger than the second radius.

As mentioned above, the tubular structure of the present invention possesses an ability to physically recover to an original state, i.e., longitudinal length and radius without elastic recovery. There is therefore no substantial elastic force exerted within said tubular structure to force it back to its relaxed state when the tubular structure is not in its relaxed state. There may be limited creeping back to the tube's pre-radially expanded shape over a substantial period of time, but this creep is a negligible amount. The tubular structure may be formed as an extruded tube or maybe a sheet which is wrapped to form a tubular structure.

The ePTFE tubular structure of the present invention is made by the following steps. The method consists of first forming a tube of polytetrafluoroethylene, preferably by extrusion of a tube which provides longitudinally oriented fibrils in the tube. The polytetrafluoroethylene tube is then stretched to form an ePTFE tube with longitudinally oriented fibrils. A longitudinally stretched ePTFE tube is known in the art and is comprised of fibrils oriented in a longitudinal direction and nodes oriented in a circumferential direction of the tube. The ePTFE tube is then placed circumferentially exterior to a longitudinally foreshortening radially expanding mechanism. The ePTFE tube may be heated to a temperature between 86° and 650° F., and the heating acts in combination with the radial pressure exerted from the foreshortening radial expansion device stent to radially expand the tubular structure.

The ePTFE tube may be radially expanded and longitudinally foreshortened without the use of heat. It may be desirous, however, to radially expand the tube with the use of heat. Heat is applied in order to facilitate the radial expansion. The temperature and time applied will vary with different types of ePTFE tubes. Generally, the thicker the wall of the tubular structure, the more heat is desirous. The heat applied is generally in the range of 86° F. and 650° F., preferably in the range of 200° F. to 500° F., and most preferably about 200°–350° F.

The method of making the ePTFE tubular structure of the present invention entails several stages during the process. The advancement of the physical treatment depends on temperature, time, and pressure in treating the ePTFE tube. Initially, the heat and outwardly exerted radial pressure dilate the tubular structure. The initial dilation of the tube coincides with a straightening of the longitudinally oriented fibrils, and then a hingeable rotation of the fibrils. This is accompanied by a circumferential shifting of the nodes along a circumferential axis; e.g. rather than a change in shape of the nodes, or lengthening of the nodes, they shift in position allowing the hingeable rotation of the fibrils. The average inter-nodal distance is shortened during this stage.

The first initial phase may be accomplished with minimal heat and in a short time frame. The actual time and heat depend on the wall thickness of the tube. With the additional radially expansive force applied to bring the tube to a larger diameter, as well as with possible additional heat for treating the ePTFE, a second phase occurs. As the dilation of the ePTFE continues, the nodes actually begin to lengthen circumferentially. The nodes lengthen with additional time, pressure and temperature. The nodes are lengthened to a second length at first in a manner that they may substantially recover to their first length. The fibrils of the ePTFE tubes become more skewed as the nodes lengthen. The reoriented fibrils provides the ePTFE tubular structure with increased longitudinal elongation and radial expansion as well as physical recovery properties. The average internal distance continues to decrease throughout the tube as you continue this radial expansive force.

With still additional treatment with heat, time and pressure, the nodes are eventually inelastically stretched, and the fibril lengths are substantially lengthened. With still further treatment, the nodes will further stretch and deform. The nodes eventually will rupture and form circumferentially oriented fibrils. In cases where such further treatment is performed, some decrease in the enhanced elongation and recovery properties may occur, but still be useful for specific applications.

The longitudinally foreshortening and radially expanding mechanism may be a number of different devices. In a preferred embodiment a wire braid may be used. In a still further embodiment a braided stent may be used. The radially exerted outward force from the foreshortening expansion mechanism is a relatively slight force which causes the fibrils to become hingeably rotated about the nodes. In the preferred embodiment, the radial pressure does not substantially deform the ePTFE tubular structure, and is applied in conjunction with heat. The tubular structure is heated to a temperature of between about 86° F. and about 650° F. Preferably the method is performed at a temperature of about 200°–350° F. The radially outwardly exerted force also causes a longitudinal shrinking in the ePTFE tubular structure.

When heat is used, the ePTFE tubular structure is allowed to cool subsequent to the heat treatment in the radially expanded and longitudinally shortened state with the removal of the heat source. The newly formed ePTFE tubular structure is therefore in a relaxed state while radially expanded and longitudinally shortened. The tube may be longitudinally lengthened and radially compressed however i.e., into its loading diameter when implanting the tubular structure. The tubular structure may be used as an endovascular graft, and preferably is used in conjunction with a stent as a covered stent or stent/graft.

In a still further embodiment of the present invention, a pre-treatment is performed on the expanded polytetrafluoroethylene tube to produce a tube with even greater elongation and recovery properties. Polytetrafluoroethylene material which has been longitudinally expanded, or ePTFE, may be "shrunk back" after the expansion process. This process entails suspension of the ePTFE material in an oven with heat. The oven is heated to a temperature generally of between about 100° F. and about 700° F. Preferably, the oven is heated to a temperature of between about 400° F. and about 500° F., and most preferably to a temperature of about 400° F.

The ePTFE material shrinks back during the heating process. The shrinking correspondingly reduces porosity of the ePTFE material, and increases the density of the ePTFE, which also decreases the length of the tube. The shrink-back procedure may shrink back the ePTFE material a significant amount. The amount the ePTFE tube may be shrunk back depends on the amount of its longitudinal expansion. The more the tube has been expanded the more it may be shrunk back. The ePTFE tube may be shrunk back up to about 125% length of the green tube; i.e., 25% greater than the original green tube length. This is generally considered the lower limit of the length to which the tube may be shrunk back; i.e. anywhere from 125% length of the green tube up to 200%, 300%, 400%, 500%, 600%, etc. of the length of the green tube before longitudinal expansion; depending on the percent of the green tube was longitudinally expanded to. The amount of shrink back depends on the length of time and temperature the ePTFE is heated in the oven.

The shrink-back procedure relaxes the fibrils of the ePTFE structure. The fibrils which were previously held taught are now relaxed and the fibril length shrinks. The nodes of the ePTFE structure are correspondingly substantially thickened by the shrink-back procedure. With the relaxed fibrils and the thickened nodes, the ePTFE structure is now more flexible and compliant than the original structure. This allows further treatment on the ePTFE to produce a structure with more structural integrity and increased tensile strength because of the more stable node and fibril structure. It allows any further treatment to more uniformly stretch or impact on the ePTFE than previously practiced in the art. The shrink-back treatment may also be referred to as fibril relaxation.

The shrink-back pre-treatment also increases the axial elongation and radial expansion propensity of the ePTFE tubular structure, i.e., the more it is shrunk back, the greater the effect.

In a still further embodiment, an additional layer may be added to a composite stent/graft device which is not extruded ePTFE. Preferably, the additional layer possesses similar capabilities of longitudinal and radial expansion and recovery. The additional layer may be a tubular textile graft, such as a knitted graft which may be attached to the stent or the extruded ePTFE layer by a number of means. For example, a tubular knitted graft may have a pattern of interlaced yarns arranged in a resilient knit pattern which permits longitudinal expansion or contraction consistent with the longitudinal expansion or contraction of the extruded ePTFE and/or stent. Although knitted textile grafts are desirable for use in conjunction with the present invention due to their ability to longitudinally expand, other textile patters such as braided patterns or even expandable woven patterns.

In order to achieve such a degree of longitudinal expansion or contraction the textile graft would be comprised of a resilient knit pattern. In one aspect the resilient pattern is a warp knitted pattern having a yarn diagonally shifted over one or more yarns in the course direction to form a loop between engaging yarns. Furthermore, the engaging yarns alternately form open loops where engaging yarns do not cross over themselves and closed loops where engaging yarns cross over themselves. Such a resilient knit pattern is described as Atlas and modified Atlas knit patterns.

In another aspect the resilient pattern is a warp knitted pattern having sets of yarns diagonally shifted over two or more yarns before forming a loop between engaging yarns. Such a resilient pattern is a warp knit pattern with at least a two needle underlap. Such patterns depart a high degree of flexibility and stretchability to the textile graft. Such knit patterns can be seen in the commonly assigned applications titled "Low Profile, High Stretch, Low Dilation Knit Prosthetic Device" and "Low Profile, High Stretch Knit Prosthetic Device", filed on the same date as the presently filed application. The applications have Attorney Docket Nos. 498-257 and 498-258, respectively and are herein incorporated by reference.

While there have been described what are presently believed to be the preferred embodiments of the invention, those skilled in the art will realize that changes and modifications may be made thereto without departing from the spirit of the invention, and it is intended to include all such changes and modifications as fall within the true scope of the invention.

What is claimed is:

1. An ePTFE tubular structure formed from the steps comprising longitudinally expanding a PTFE tubular structure to provide a first node and fibril orientation and subjecting said first node and fibril orientation to a radially expansive and longitudinal foreshortening force to form a second node and fibril orientation whereby fibrils have been hingeably rotated about the nodes in a relaxed state, wherein fibril line segments of said second fibril orientation are not substantially changed in dimension from corresponding fibril line segments of said first fibril orientation and further wherein said ePTFE tubular structure is an extruded tubular structure.

2. The tubular structure as described in claim 1 wherein said tubular structure possesses enhanced longitudinal elongation and radial expansion properties.

3. The tubular structure as described in claim 1 wherein said fibrils possess a length which is not substantially changed in said second orientation.

4. The tubular structure as described in claim 1 wherein said tubular structure possesses a first longitudinal length and a first radius in a relaxed state and a second longitudinal length and second radius wherein said second longitudinal length is greater than said first longitudinal length and said second radius is less than said first radius.

5. The tubular structure as described in claim 4 wherein said second longitudinal length is at least about 1.5 times longer than said first longitudinal length.

6. The tubular structure as described in claim 5 wherein said second longitudinal length is at least about 2.0 times longer than said first longitudinal length.

7. The tubular structure as described in claim 6 wherein said second longitudinal length is at least about 2.5 times longer than said first longitudinal length.

8. The tubular structure as described in claim 4 wherein said first radius is at least about 1.5 times larger than said second radius.

9. The tubular structure as described in claim 8 wherein said first radius is at least about 2.0 times larger than said second radius.

10. The tubular structure as described in claim 9 wherein said first radius is at least about 2.5 times larger than said second radius.

11. The tubular structure as described in claim 4 wherein said tubular structure is capable of returning to said first longitudinal length and said first radius in the absence of substantial elastic recovery.

12. The tubular structure according to claim 1, wherein said tubular structure is circumferentially disposed exteriorly around a tubular stent structure.

13. The tubular structure according to claim 12 wherein said stent is a braided stent.

14. The tubular structure according to claim 12 further comprising a tubular textile graft circumferentially positioned exterior to said tubular structure.

15. The tubular structure according to claim 1, wherein said tubular structure is circumferentially positioned interior to a tubular stent structure.

16. The tubular structure according to claim 15 further comprising a textile graft circumferentially disposed exteriorly around said tubular stent structure.

17. The tubular structure according to claim 1, wherein said fibrils have been hingeably rotated about the nodes by a radially outwardly exerted and longitudinally foreshortening force.

18. The tubular structure according to claim 17, wherein said radial force has been exerted by a braided stent.

19. The tubular structure according to claim 18, wherein said radial force does not substantially inelastically deform said ePTFE tubular structure.

20. The tubular structure according to claim 17, wherein said radial force is applied in conjunction with heat.

21. A longitudinally expanded polytetrafluoroethylene tubular structure comprising a node and fibril structure, wherein said fibrils have been hingeably rotated about said nodes by a radially expansive and longitudinally foreshortening force prior to longitudinal expansion of said tubular structure, wherein fibril line segments of said second fibril orientation are not substantially changed in dimension from corresponding fibril line segments of said first fibril orientation and further wherein said expanded polytetrafluoroethylene tubular structure is an extruded tubular structure.

22. A longitudinally expanded polytetrafluorethylene tubular structure comprising a hingeably rotated node and fibril structure in a relaxed state, wherein fibril line segments of said second fibril orientation are not substantially changed in dimension from corresponding fibril line segments of said first fibril orientation, said expanded polytetrafluoroethylene tubular structure is an extruded tubular structure and further wherein an inter-nodal distance is less after hingeable rotation of the fibrils.

23. An ePTFE tubular structure according to claim 22 wherein said fibril length is substantially the same.

24. A method of orientating node and fibril structure of expanded polytetrafluorethylene comprising exerting a radially expanding and longitudinal foreshortening force to a longitudinally expanded polytetrafluorethylene tubular structure to provide hingeably rotated fibril structure in a relaxed state, wherein fibril line segments of said second fibril orientation are not substantially changed in dimension from corresponding fibril line segments of said first fibril orientation and further wherein said expanded polytetrafluoroethylene tubular structure is an extruded tubular structure.

* * * * *